(12) United States Patent
Greene

(10) Patent No.: US 6,752,818 B2
(45) Date of Patent: Jun. 22, 2004

(54) STOMA DILATOR

(76) Inventor: Karen Greene, 720 Fort Washington Ave., Apt. 3C, New York, NY (US) 10040

(*) Notice: Subject to any disclaimer, the term of this patent is extended or adjusted under 35 U.S.C. 154(b) by 0 days.

(21) Appl. No.: 09/935,192

(22) Filed: Aug. 22, 2001

(65) Prior Publication Data

US 2003/0040768 A1 Feb. 27, 2003

(51) Int. Cl.$^7$ .............................................. A61M 29/00

(52) U.S. Cl. ...................................................... 606/191

(58) Field of Search .................................. 606/191, 192, 606/197, 199, 190

(56) References Cited

U.S. PATENT DOCUMENTS

| | | | | |
|---|---|---|---|---|
| 3,698,391 A | * | 10/1972 | Mahony | 606/191 |
| 3,916,906 A | * | 11/1975 | Gerry | 606/192 |
| 4,346,714 A | * | 8/1982 | Child | 606/191 |
| 5,437,649 A | | 8/1995 | Letchworth | 604/278 |
| 5,681,340 A | * | 10/1997 | Veronikis | 606/191 |

\* cited by examiner

*Primary Examiner*—Kevin T. Truong
(74) *Attorney, Agent, or Firm*—Woodcock Washburn LLP

(57) ABSTRACT

A stoma dilator for insertion into an opening formed in the human body comprises a base and an insert integrally formed with said base and extending there from. The insert has a tapered portion near said base that operates to maintain the diameter of the opening as well as hold the stoma dilator in place in the opening.

17 Claims, 1 Drawing Sheet

STOMA DILATOR

FIELD OF THE INVENTION

The present invention relates generally to medical devices, and more particularly, to medical devices for use by patients having surgically created stomas.

BACKGROUND OF THE INVENTION

Numerous surgical procedures result in the creation of a stoma, or surgically created opening in the body. For example, patients who undergo a cystectomy, which is the surgical removal of the bladder, may have a stoma created, usually in the abdomen wall or navel, to allow the passage of urine to the outside of the body from an internal reservoir. In the context of surgical procedures, such as a cystectomy, the stoma, with its attached internal conduit, is typically made to have a diameter that is operable with or matches a standardized catheter diameter size, as the patient will need to insert such a catheter several times daily in order to void.

Surgically created stomas often shrink during the recovery period, making the insertion of devices such as catheters difficult and painful for the patient. Also, there is an increased risk of urinary tract infection if irritation occurs due to repeated insertions over and through contracted or swollen tissues. Indeed, the irritation may become so acute that bleeding may result.

Accordingly, there is a need in the art for a device for maintaining the diameter, and minimizing the shrinkage of surgically created stomas.

SUMMARY OF THE INVENTION

Generally, Applicant has invented a stoma dilator that addresses these needs in the art.

According to an aspect of the invention, a stoma dilator is disclosed comprising a base and an insert integrally formed with the base and extending therefrom. The insert is inserted into the stoma while the base remains exterior to and abuts the body tissue surrounding the stoma. The girth of the insert increases at the portion of the insert that corresponds to the stoma entry location so as to be of sufficient size to maintain the desired stoma diameter and thereby prevent shrinkage. According to an aspect of the invention, the base is formed so as to create suction pressure between the dilator and the portion of the body surrounding the stoma and thereby provide additional securing forces between the dilator and the stoma.

A stoma dilator in accordance with the invention may be inserted into a patient stoma overnight or any other period so as to maintain the size of the stoma.

Additional aspects of the invention are described in detail below.

BRIEF DESCRIPTION OF THE DRAWINGS

Other features of the invention will be further apparent from the following detailed description of presently preferred exemplary embodiments of the invention taken in conjunction with the accompanying drawings, of which.

DETAILED DESCRIPTION OF THE INVENTION

Figure 1:
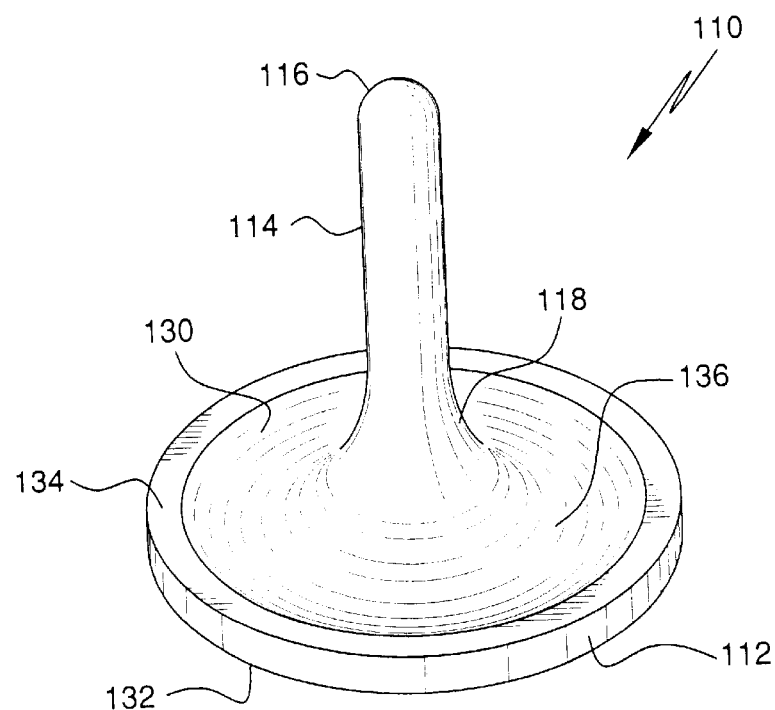
FIG. 1 is perspective view of a stoma dilator in accordance with an aspect of the present invention.

A stoma dilator with the above-mentioned beneficial features in accordance with a presently preferred exemplary embodiment of the invention will be described below with reference to FIGS. 1 and 2. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

According to an aspect of the invention, a stoma dilator for maintaining the diameter of surgically created stomas is provided. FIG. 1 provides a perspective view of stoma dilator 110 in accordance with the invention. As shown, stoma dilator 110 comprises base 112 and insert 114 extending there from. In the exemplary embodiment, insert 114 and base 112 are integrally formed. Insert 114 is designed to be positioned in the patient's stoma while base 112 remains exterior to the body and abuts the tissue surrounding the stoma. Insert 114, when inserted into the stoma, maintains the size of the stoma and prevents it from shrinking.

In the exemplary embodiment, insert 114 has a circular cross section and a generally cylindrical shape. Insert 114 may have cross sections corresponding to other shapes such as, for example, an oval or egg, depending on the shape and use of the stoma into which the insert 114 will be placed.

The girth of insert 114 may be designed to correspond to a particular application. For example, in applications for use with cystectomy patients wherein the stoma accepts a catheter, insert 114 has a girth approximately equivalent to the catheter that is accepted into the stoma. Insert 114 may be sized to correspond to the various standard urinary catheter sizes.

Distal end 116 of insert 114 is tapered so as to facilitate entrance of insert 114 into a stoma. Notably, distal end 116 does not have any urine collection eyes such as are typically incorporated in catheters and which may cause stoma abrasion upon insertion and removal.

At dilator end 118 of insert 114, the girth of insert 114 increases, resulting in insert 114 tapering outward near its intersection with base 112. The increased girth at dilator end 118 provides for added resistance between insert 114 and the tissues of the stoma. The increased resistance operates to maintain the diameter of the stoma entrance as well as to keep stoma dilator 110 lodged in the stoma.

The length or height of insert 114 may vary depending upon the size and use of the target stoma. For example, for stomas used in connection with catheterization, the length of insert 114 may vary from about one inch to six inches depending on the needs of the particular patient, so as to remain in the conduit, outside of the urine reservoir.

As shown in FIG. 1, base 112 comprises a first side 130, which is referred to herein as the internal side, and a second side 132, which is referred to herein as the external side. In the exemplary embodiment, base 112 has a generally circular shape. Of course, other shapes may be used such as, for example, a square or an oval.

Interior side 130 has a rim 134 formed around its perimeter. Area 136 of interior side 130 between rim 134 and insert 114 has a concave shape such that when dilator insert 110 is placed in a stoma, and base 112 comes into contact with the body area surrounding the stoma, suction pressure may be formed between dilator insert 110 and the body. This suction pressure fortifies the position of dilator insert 110 in the stoma.

Exterior side 132 is generally smooth and has a convex shape. Alternatively, exterior side 132 may have a ridge, handle, or other structure formed therein to facilitate inserting and removing dilator insert 110 from a stoma.

Figure 2:
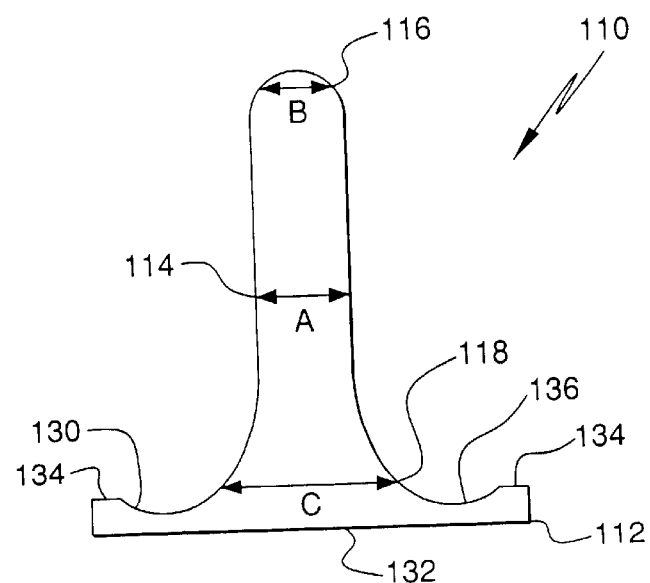
FIG. 2 is sectional view of a stoma dilator in accordance with an aspect of the present invention.

FIG. 2 provides a cross sectional view of stoma dilator 110 and illustrates the widths of insert 114 at various locations along its length. As shown, near its middle, and along a portion of its length, insert 114 has a width A. Near distal end 116, insert 114 tapers down to width B. The reduced width facilitates insertion of dilator insert 110 into a stoma.

At dilator end 118 the width of insert 114 increases to C. The increased width at dilator end 118 provides for added resistance between insert 114 and the tissues of the stoma. The increased resistance operates to maintain the diameter of the stoma entrance as well as to keep stoma dilator 110 lodged in the stoma.

FIG. 2 also illustrates concave area 136 of insert side 130 that is formed between rim 134 and insert 112. When rim 134 is placed in contact with a body, suction pressure may be formed between dilator 110 and the body.

Generally, dilator insert 110 is sufficiently rigid to maintain the diameter of a stoma. However, dilator insert 110, and particularly insert 114 may be flexible in order to fit the curves or contours of the conduit formed inside the body behind the stoma.

Dilator insert 110 is composed of materials that are suitable for insertion into the human body. For example, dilator insert 110 may be composed of polyvinyl chloride (PVC), latex rubber, silicone, and similar materials that are typically used in catheter devices. Dilator insert 110 may be either solid or have a hollowed tube design which comes to a distal closed tip.

Thus, there has been disclosed a stoma dilator for maintaining the diameter, and minimizing the shrinkage of surgically created stomas. The inventive stoma dilator reduces shrinkage in stomas and thereby helps prevent irritation and complications resulting therefrom. In contrast to catheters, the stoma dilator comprises an outwardly tapered dilator end for maintaining the desired size of the stoma and securing the dilator in the stoma, and a self-adhering base for providing additional force to secure the dilator in the stoma. Furthermore, in contradistinction to catheters, the distal end of the stoma dilator has no urine collection eyes which may cause abrasion upon insertion and removal.

A patient may insert a stoma dilator in accordance with the invention into a stoma and leave the stoma insert in the stoma for extended periods of time so as to maintain the size of the stoma. For example, cystectomy patients that have a stoma through which they void may insert a stoma dilator in accordance with the invention in the stoma so as to maintain the size of the stoma between voiding. The patient may leave the stoma dilator in the stoma between voidings for several hours or as directed by a physician. Upon removal of the stoma dilator, a patient may insert a catheter in order to void.

While the invention has been described and illustrated with reference to specific embodiments, those skilled in the art will recognize that modification and variations may be made without departing from the principles of the invention as described above and set forth in the following claims. For example, insert and base may have shapes and configurations other than that depicted. Accordingly, reference should be made to the appended claims as indicating the scope of the invention.

What is claimed is:

1. A stoma dilator for insertion into an opening formed in the human body, comprising:

a base; and an insert integrally formed with said base and extending there from, said insert having an outwardly tapered portion at the intersection of said insert with said base;

wherein said base has a first side from which said insert extends and a second side opposite said first side, said first side having a rim along its perimeter and a concave region between said rim and a portion of said first side from which said insert extends.

2. The stoma dilator of claim 1, wherein said second side has a smooth convex surface.

3. The stoma dilator of claim 1, wherein when said first side is operable to form an area of suction between said stoma dilator and the human body into which the stoma dilator is inserted.

4. The stoma dilator of claim 1, wherein said insert has a circular cross-section.

5. The stoma dilator of claim 4, wherein the diameter of said circular cross-section increases across a length of said insert near said base.

6. The stoma dilator of claim 4, wherein the diameter of said circular cross-section decreases across a length of said insert near said distal end.

7. The stoma dilator of claim 1, wherein said insert is between about 1 inch and 6 inches in length.

8. The stoma dilator of claim 1, wherein said stoma dilator is composed of rigid plastic.

9. The stoma dilator of claim 1, wherein said stoma dilator is composed of flexible plastic.

10. The stoma dilator of claim 1, wherein the girth of said insert is about equal to the girth of a standard catheter.

11. A stoma dilator for insertion into an opening formed in the human body, comprising:

a base; and an insert integrally formed with said base for insertion into the opening, the girth of said insert decreasing near a first end for facilitating entrance of said insert into the opening, and the girth of said insert increasing near a second end at the intersection of said insert with said base for maintaining a diameter of the opening and securing the insert in the opening, wherein said base has a first side from which said insert extends and a second side opposite said first side, said first side having a rim along its perimeter and a concave region between said rim and a portion of said first side from which said insert extends.

12. The stoma dilator of claim 11, wherein said second side has a smooth convex surface.

13. The stoma dilator of claim 11, wherein said first side is operable to form an area of suction between said stoma dilator and the human body into which the stoma dilator is inserted.

14. The stoma dilator of claim 11, wherein said second side has a ridge formed therein for facilitating inserting and removing said stoma dilator from the opening.

15. The stoma dilator of claim 11, wherein said stoma dilator has a circular cross sectional area.

16. A stoma dilator for maintaining an opening in a human body, comprising a base integrally formed with an insert, wherein said insert tapers outwardly at its intersection with said base for interacting with the tissue forming the opening, wherein said base has a first side from which said insert extends and a second side opposite said first side, said first side having a rim along its perimeter and a concave region between said rim and a portion of said first side from which said insert extends.

17. The stoma dilator of claim 1, wherein said insert has a tapered distal end.

* * * * *